United States Patent [19]

Buter

[11] Patent Number: 5,043,438

[45] Date of Patent: Aug. 27, 1991

[54] PROCESS FOR THE SYNTHESIS OF POLYOL FATTY-ACID ESTERS

[75] Inventor: Markus G. Buter, Vlaardingen, Netherlands

[73] Assignee: Van den Bergh Foods Co., Division of Conopco Inc., Lisle, Ill.

[21] Appl. No.: 477,776

[22] Filed: Feb. 9, 1990

[30] Foreign Application Priority Data

Feb. 16, 1989 [EP] European Pat. Off. ........ 89200371.6
Nov. 20, 1989 [EP] European Pat. Off. ........ 89202931.5

[51] Int. Cl.$^5$ ...................... C07H 13/00; C07H 1/00; C11C 3/00
[52] U.S. Cl. .................... 536/119; 536/115; 536/120; 536/124; 260/410.7
[58] Field of Search ............... 536/119, 115, 120, 124; 260/410, 410.7

[56] References Cited

U.S. PATENT DOCUMENTS

| | | |
|---|---|---|
| 4,517,360 | 5/1985 | Volpenhein .......................... 536/119 |
| 4,518,772 | 5/1985 | Volpenhein .......................... 536/119 |
| 4,968,791 | 11/1990 | Van Der Plank .................. 536/119 |
| 4,973,682 | 11/1990 | Willemse ............................. 536/119 |

*Primary Examiner*—Ronald W. Griffin
*Assistant Examiner*—Everett White
*Attorney, Agent, or Firm*—Gerald J. McGowan, Jr.

[57] ABSTRACT

The present invention pertains to a process for the synthesis of polyol fatty-acid esters by reacting a polyol and a fatty-acid lower-alkyl ester under substantially solvent-free conditions in the presence of a transesterification catalyst and an emulsifier. The process comprises a continuous initial reaction stage in a first reaction zone wherein a steady-state conversion is achieved of over 1% and a further reaction stage in which the reaction mixture from said first zone is further reacted to the required polyol fatty-acid esters in one or more subsequent reaction zones.

21 Claims, No Drawings

PROCESS FOR THE SYNTHESIS OF POLYOL FATTY-ACID ESTERS

The present invention relates to a process for the synthesis of polyol fatty-acid esters by reacting a polyol and a fatty-acid lower-alkyl ester under substantially solvent-free conditions in the presence of a transesterification catalyst and an emulsifier. Although applicable to the synthesis of the general group of polyol fatty-acid esters, the invention is particularly directed to the synthesis of polyol fatty-acid polyesters.

In this specification the term "polyol" is intended to include any aliphatic or aromatic compound which comprises at least four free hydroxyl groups. In particular such polyols include the group of sugar polyols, which comprise the sugars, i.e. the mono-, di- and polysaccharides, the corresponding sugar alcohols and the derivatives thereof having at least four free hydroxyl groups. Examples of sugar polyols include glucose, mannose, galactose, xylose, fructose, sorbose, tagatose, ribulose, xylulose, lactose, maltose, raffinose, cellobiose, sucrose, erythritol, mannitol, lactitol, sorbitol, xylitol and $\alpha$-methylglucoside. A generally used sugar polyol is sucrose.

In this specification the term "polyol fatty-acid ester" is intended to include both the group of polyol fatty-acid oligoesters, in particular the mono-, di- and trifatty-acid esters, and the group of polyol fatty-acid polyesters, i.e. the tetra- up to the fully fatty-acid esterified polyols.

In this specification the percentage of polyol hydroxyl groups of the original polyol that on an average have been esterified with fatty acids, is referred to as the degree of polyol conversion, a degree of polyol conversion of 100% corresponding to the fully esterified polyol.

In this specification the term "fatty acid" refers to $C_8$–$C_{24}$ fatty acids which may be saturated or unsaturated, and may have straight or branched alkyl chains.

The polyol fatty-acid oligoesters are well-known for their suitablility as emulsifying agents in foodstuffs and detergents, and as drying oils in paint and varnish.

The polyol fatty-acid polyesters are known to be suitable low-calorie fat-replacers in edible products. Substantially indigestible for human beings they have physical and organoleptic properties very similar to triglyceride oils and fats conventionally used in edible products. Polyol fatty-acid polyesters are further reported to have use as pharmaceutical agents in view of their ability to take up fat-soluble substances, such as in particular cholesterol, in the gastro-intestinal tract, and subsequently remove these substances from the human body.

Processes for the synthesis of polyol fatty-acid esters using transesterification reactions in substantially solvent-free systems are well known. Examples of such processes are described e.g. in U.S. Pat. Nos. 3,963,699, 4,517,360, 4,518,772 and European Pat. Nos. 0 256 585, 0 254 376 and 0 301 634.

One of the main problems in prior art syntheses of polyol fatty-acid esters is caused by the heterogeneous nature of the reactant mixture at the start of the transesterification reaction. The considerable differences in polarity between the various reactants may cause partial or full de-mixing of the reactant mixture, which is very undesirable in general, but prohibitive to processes on a technical scale.

To reduce the problem of de-mixing of the reactants and to have the full amounts of reactants participate in the transesterification reaction in most cases an emulsifier is required to get a macroscopically homogeneous starting mixture. To this purpose particularly soap emulsifiers are used.

However, in conventional esterification processes on a technical scale the use of soap is frequently accompanied by viscosity problems which depending on the specific soap used may occur at introduction of the soap or the fatty acids used to produce the soap, into the reaction mixture as also at the final stages of the esterification reaction, i.e. at high degrees of conversion.

It is now an object of the present invention to provide an improved process for the synthesis of polyol fatty-acid esters, particularly with respect to avoiding initial viscosity and/or de-mixing problems, which is applicable on a technical scale.

It has now been found that the above problems which particularly occur in the very initial stage of the reaction at very low degrees of polyol conversion, can be substantially overcome by carrying out the first part of the transesterification reaction in a continuous manner. Instead of batchwise starting each esterification process from a mix of unconverted polyol and fatty-acid lower-alkyl ester, the initial part of the reaction is carried out in a continuous manner by achieving, in a first reaction zone, a steady-state polyol conversion of over about 1% and mass-balancing under suitable reaction conditions one or more in-going reactant streams of polyol and fatty-acid lower-alkyl ester and out-going product streams of reaction mixture comprising partially converted polyol, and of lower-alkyl alcohol formed in the initial conversion. In this first zone, on an average, the polyol conversion is progressed to beyond the point where de-mixing and high viscosities occur, the steady-state reaction mixture in said first zone being capable of homogenizing and solubilizing said in-going streams of reactants.

It has further been found that by carrying out at least the initial part of the transesterification in a continuous manner, once the process has been started and is in steady-state only relatively low amounts of emulsifier are needed. The viscosity problems during the final stages of the transesterification reaction and the associated problem of refining the polyol (poly)ester product are therefore also avoided or significantly reduced.

Accordingly, the invention provides a process for the synthesis of polyol fatty-acid esters by reacting a polyol and a fatty-acid lower-alkyl ester under substantially solvent-free conditions in the presence of a transesterification catalyst and an emulsifier, said process comprising an initial reaction stage (a) which is carried out in a first reaction zone under such conditions that the reaction mixture in said first zone is in steady-state with mass-balanced one or more in-going reactant streams into said first zone and out-going product streams from said first zone, said one or more in-going reactant streams comprising polyol and fatty-acid lower-alkyl ester, and said out-going product streams comprising reaction mixture having a polyol conversion of 1% or more and lower-alkyl alcohol formed during the initial stage of the synthesis, and a subsequent reaction stage (b) in which the reaction mixture from said first zone, optionally after combining with any remaining part of reactants, is further reacted to said polyol fatty-acid esters in one or more subsequent reaction zones.

This first reaction zone may be a reaction vessel fully separate from one or more further reaction vessels, but it may also be part of multi-zone continuous esterification equipment. Such multi-zone continuous esterification equipment may consist of a serial sequence of separate reaction vessels as also of e.g. a multi-tray column reactor with cross-flow or counter-current stripping equipment, or a combination thereof.

The reactants which are fed to the first reaction zone on a continuous basis and in mass balance with the out-going product streams from this first zone, are a polyol and a fatty-acid lower-alkyl ester. The polyol and the fatty-acid lower-alkyl ester may be introduced into the first reaction zone as separate streams, but are generally and preferably combined in a single in-going stream.

Under steady-state conditions the one or more in-going reactant steams of polyol and fatty-acid lower-alkyl ester should be in mass balance with the out-going product streams of the reaction mixture comprising the partially converted polyol, and of lower-alkyl alcohol formed during the initial reaction stage. In the first reaction zone steady-state polyol conversions should be achieved of over 1%, and in general suitable conversions lie within the range of from 2 to 60%, in particular, 3 to 50%. Polyol conversions of over 60% in the first reaction zone in general carry a prohibitive cost penalty. Preferred steady-state polyol conversions lie within the range of from 10 to 40%, and conversions of within the range of 15 to 30 or even to 25% have been found to give best results.

The polyol can be any of those as defined hereinbefore, or a mixture thereof. Preferred polyol starting materials are the sugar polyols, and in particular sucrose.

Suitable fatty-acid lower-alkylesters are fatty-acid esters of the group of lower alcohols including mono-, di- and triols. In particular, the ester is derived from the $C_1$-$C_5$ mono-alcohols, preferably methanol. The fatty-acid residues can be any of those as defined hereinbefore, the selection of which is dependent of the specific polyol fatty-acid esters desired.

The amount of fatty-acid lower-alkylester is dependent on the desired degree of conversion. In general excess amounts of fatty-acid lower-alkylester are used. More particularly, when fully converted sucrose polyesters are aimed at, good results are obtained when a molar ratio of fatty-acid lower-alkylester:sucrose is used within the range of from 10:1 to 20:1, and preferably of from 10.5:1 to 18:1, or even from 10.5:1 to 14:1.

It is not necessary to introduce the full amount of all the reactants, in particular the fatty-acid lower-alkyl ester, into the first reaction zone, but part may also be added to the reaction mixture at a later stage of the transesterification reaction. Particularly, in the synthesis of polyol fatty-acid polyesters having very specific fatty-acid compositions, e.g. a combination of two or more sharp fatty-acid fractions, addition of different fractions of fatty-acid lower-alkyl esters corresponding to such sharp fatty-acid fractions during later stages of the esterification reaction may be desirable or necessary.

Suitable transesterification catalysts include the group consisting of alkali metals, alkaline earth metals, and alloys thereof, as well as the alkoxides, bicarbonates, carbonates, hydrides, and hydroxides of such metals. KOH has been found to be particularly suitable, but also NaOH and the corresponding carbonates, and bicarbonates of potassium or sodium can be advantageously used. Although one might argue that the above reagents are not the catalysts themselves, but are reagents forming the catalyst, in this specification as is done in the literature relating to similar processes, this group will be referred to as catalysts.

In general the catalyst is introduced into the first reaction zone as part of the in-going stream containing the polyol. Part of the polyol will have reacted with the catalyst under formation of the polyol anion which in the reaction is believed to be the actual catalyzing agent.

The catalyst is used in an amount corresponding to a molar ratio of catalyst:polyol of at least 0.01:1, and in particular of within the range of 0.05:1 to 1:1. Preferred catalyst:polyol ratios lie within the range of 0.1:1 to 0.3:1, best results having been found with ratios within the range of from 0.2:1 to 0.3:1.

During the start-up of the process in accordance with the present invention an emulsifier should be introduced to improve contact between the various reactants particularly in said first reaction zone. Many types of alkali-resistant emulsifiers can suitably be used, such as edible emulsifiers including phosphatides, such as lecithin, mono- and diglycerides and sugar oligoesters of fatty acids, in particular the mono- and diesters, and detergents, such as soaps and alkali metal alkyl sulphates.

Preferred emulsifiers are alkali metal soaps derived from any of the fatty acids as defined hereinbefore. It has been found that conversion rates of polyol to polyol fatty-acid ester are improved as also any viscosity problems during the final stages of the esterification reaction are avoided when fatty-acid soap emulsifiers are used comprising at least 15% by weight short-chain fatty acid soaps. Preferred levels of short chain fatty-acid soap are 75 to 100% by weight. Such short chain fatty-acid soaps are characterized by a fatty-acid chain lengths of less than 15 carbon atoms, and in particular within the range of 6 to 14 carbon atoms, such as coconut soap.

Suitable amounts of emulsifier in the first reaction zone in general lie within the range of from 0.1 to 15% by weight of the total reactant mixture, and in particular, of from 0.2 to 12%, amounts of 1 to 4% by weight being preferred. At the start-up of the reaction such amounts of emulsifier are introduced into the first reaction zone preferably as part of the one or more in-going reactant streams of polyol and lower-alkyl fatty-acid ester, during steady-state conditions in the first reaction zone the emulsifier may also be introduced by recirculation from further stages of the esterification reaction. The molar ratio of emulsifier to polyol during steady-state conditions in the first reaction zone preferably is within the range of 0.2:1 to 0.8:1, molar ratios of 0.3:1 to 0.7:1, such as about 0.4:1 being preferred most.

Particularly, when the emulsifier is selected from the group of alkali metal soaps, it may be convenient, before introduction into the first reaction zone, to first dissolve the corresponding fatty acids in the lower-alkyl fatty acid ester and neutralize with an alkaline material, such as KOH.

Optionally, before introduction of the various components into the first reaction zone one or more solvents may be used to improve addition and mixing thereof. Suitable solvents include water and/or lower alcohols, such as $C_1$-$C_5$ alcohols, in particular methanol.

It is an essential feature of the processes in accordance with the present invention that before introduction into the first reaction zone any such solvents are substantially removed to achieve in the first reaction zone substantially solvent-free reaction conditions.

By substantially solvent-free reaction conditions is meant less than 0.5% by weight of solvent, in particular of water. In principle solvent levels at the start-up of the transesterification reaction should be as low as possible, but to some extent will be determined by economic considerations. Solvent levels of less than 0.1% by weight and particularly of from 0.01% to 0.08% by weight are preferred, effecting levels of below 0.01% by weight getting prohibitively expensive.

De-solvatizing of the various components or component mixes may be suitably achieved by way of spray-drying which may be carried out at introduction into the first reaction zone, but preferably before such introduction, by passing the mixture through a spraying nozzle under drying conditions.

It may be of further advantage to pre-homogenize streams of combined components fed to the first reaction zone before the passing thereof through the spraying nozzle by an alternative agitation step for example employing a dynamic or static mixer, or flow restriction in the feed line to the spraying nozzle.

Preferably, in the first reaction zone agitation is applied to ensure thorough mixing of the reaction components and to aid the removal of the lower-alkyl alcohols which are formed during the transesterification reaction. Such agitation is suitably achieved by stirring.

The streams of reactants to and from the first reaction zone should be such that under the temperature and pressure conditions described hereunder in more detail, the average residence time of the reaction mixture in the first zone is caused to be within the range of 1 to 4 hours, in particular of 1.2 to 3 hours. To minimize the risk of non-participating polyol average residence times in the range of from 1.5 to 2.5 are preferred, best results being obtained using residence times in the range of from 1.7, and particularly 1.8, to 2.2 hours.

In accordance with the process of the present invention the out-going reaction mixture from the first reaction zone is subsequently further reacted under suitable conditions to cause transesterification to the desired polyol fatty-acid esters. This may be carried out both batch-wise or continuously.

In general, the transesterification reaction both in the first reaction zone and in the subsequent further reaction is carried out at elevated temperature, in particular, in the range of from 100° to 180° C., a reaction temperature in the range of 110° to 160° C. being preferred, temperatures in the range of from 120° to 150° C. or even 130° to 140° C. being preferred most.

The reaction is carried out under such conditions that the lower-alkyl alcohols formed in the transesterification, are removed during the reaction. To this purpose the reaction is advantageously carried out at reduced pressure in terms of the partial vapour pressure of the lower-alkyl alcohol. Suitably such partial vapour pressures in the first reaction zone are reduced to levels within the range of from 20 to 200 mbar, pressures of 35 to 150 and particularly of 40 to 125 mbar being preferred. Best results are obtained with prssure levels of from 40 to 100 mbar. During the reaction subsequent to the first reaction zone pressures are applied as low as possible, such as below 50 mbar and in particular below 25 mbar. When full esterification of the polyol is aimed at, the partial vapour pressure of the lower-alkyl alcohol is preferably reduced to a level of less than 10 mbar, and most preferably to a level of less than 5 mbar. These pressures may be achieved by gradual pressure reduction over time in a batch-wise process, but also by a step-wise pressure reduction over two or more reaction compartments or zones in a continuous process.

Particularly during the final stage of a batch-wise process or in the final reaction zone of a continuous process, a preferred method to reduce the lower-alkyl alcohol partial vapour pressure is to use a stripping agent to ensure adequate removal of the lower-alkyl alcohol formed during the transesterification reaction. Suitable such stripping agents include inert gases, such as nitrogen, and volatile (under reaction conditions) organic compounds having low or no oxidating tendency. A particularly preferred stripping agent of the latter type is hexane.

Appropriate amounts of stripping agent through the reaction mixture are dependent upon the reaction conditions and the set-up and dimensions of the equipment. In general, suitable amounts of stripping agent during the final stages of the reaction lie within the range of 1000 to 4000 liters of stripping agent per kg of reaction mixture, amounts within the range of 2000 to 3000 liters/kg being preferred.

Although often suitable partial vapour pressures during earlier stages of the transesterification reaction can be achieved without the use of stripping agents, if it is desired to use stripping agents also during these stages of the transesterification reaction, only lower amounts of stripping agent are needed. Being somewhat dependent upon the molar ration of polyol versus fatty-acid lower-alkyl ester, suitable amounts of stripping agent during the initial stages preferably are selected within the range of 30 to 700 liters/kg, and in particular within the range of 60 to 300 liters/kg.

The amount of stripping agent is expressed as liters per kg of reaction mixture under the pressure and temperature conditions of the reaction mixture at the moment of stripping.

Suitable contact between the stripping agent and the reaction mixture is normally established due to the whirling action caused by the stripping agent flowing through the reaction mixture. However, it may be desirable to apply further agitation by way of appropriate stirrer means.

Preferably, after leaving the reaction mixture the stripping agent is first, at least partly, separated from the lower alkyl alcohol, and subsequently recirculated to the reaction mixture.

Although the process of the present invention is suitable for the synthesis of both polyol fatty-acid oligoesters and polyesters as defined hereinbefore, it is particularly directed to the synthesis of the polyester group. The polyesters will in general be characterised by a degree of polyol conversion of 70% or more, degrees of polyol conversion of 80% or more, or even of 90% or more being preferred. In particular, such polyesters derived from the sugar polyols selected from the group of disaccharides or the alcohol derivatives thereof, such as sucrose, and esterified to a degree of polyol conversion of 95% or more, or even of 98% or more, are suitably and preferably synthesized by the method in accordance with the present invention.

The invention will now be illustrated more specifically in the following experimental examples.

Where a full synthesis was tested the processes described in the following examples were carried out in a reactor configuration consisting of a pre-reactor and a main reactor.

The pre-reactor (which corresponds to the first reaction zone in accordance with the invention) consisted of a cylindrical reaction vessel provided with means for stirring and heating, in- and outlets for stripping agent, a peristaltic-pump driven feed for the in-going stream of reactants and a peristaltic-pump driven suction line for the out-going product stream of reaction mixture from the pre-reactor to the main reactor. The inlet point of the suction line in the pre-reactor was such that all fluids above a certain point were removed.

As the main reactor a three-tray column reactor with means for heating and counter-current stripping was used.

In the examples 1 to 11 the polyol was sucrose, the transesterification catalyst was potassium hydroxide, the emulsifier was the potassium soap of coconut fatty acids and the fatty-acid lower-alkyl ester was the methanol ester of fatty acids derived from partially hardened soybean oil (hardened to a melting point of 28° C.). These reactants were introduced in the pre-reactor in the form of a single stream formed by combining a concentrated slurry (about 10–15%) of the coconut soap in part of the soybean methanol ester with a sucrose/KOH dispersion (about 10%) in the remainder of the soybean methanol ester.

In both the pre-reactor and the main reactor partial methanol pressures were reduced by way of stripping. As stripping agent nitrogen gas was used.

In the examples all percentages are expressed by weight of the total reaction mixture unless indicated otherwise.

EXAMPLE 1

The reactant feed to the pre-reactor consisted of:
sucrose: 6.24%
KOH: 0.27%
soap (*): 3.13%
soybean methanol ester: 90.30%
water: 0.06%
(*) 2.8% of coconut soap plus 0.3% of soybean soap due to partial conversion of the soybean methanol ester.

In terms of molar ratios these amounts corresponded to:
KOH:sucrose—0.27:1
soap:sucrose—0.65:1
soybean methanol ester:sucrose—16.7:1

The reaction conditions in the pre-reactor (volume about 1 liters) were:
temperature: 135° C.
partial methanol pressure: 55 mbar
stirring power input per volume of reaction mixture: 4–5 W/l
stripping gas volume per weight of reactant feed: 149 l/kg (*)
average residence time of reaction mixture in pre-reactor: 1.8 hours
(*) under reaction conditions Reaching steady-state in about 2.5 average residence times after start-up, the composition of the out-going product stream of reaction mixture from the pre-reactor which was fed to the first compartment of the main reactor, was:
sucrose oligoester (degree of conversion: 16.7%): 12.71%
sucrose: 0.02%
KOH: 0.11%
soap: 3.90%
soybean methanol ester: 82.97%

The reaction conditions in the various compartments of the main reactor (total reactor volume of about 3 liters) were:

| | reactor compartments | | |
|---|---|---|---|
| | 1 | 2 | 3 |
| temperature (°C.) | 137° C. | 133° C. | 137° C. |
| average residence time (hours) | 1.7 h | 1.9 h | 2.0 h |
| partial methanol pressure (*) | 16 mbar | 5 mbar | 1 mbar |
| degree of conversion of sucrose polyester | 71.1% | 91.1% | 96.6% |

(*) stripping gas volume per weight of reactant feed 2500 l/kg

The composition of the final product from the main reactor was:
sucrose polyester (degree of conversion: 96.6%): 45.60%
sucrose: 0.00%
KOH: 0.04%
soap: 4.16%
soybean methanol ester: 49.59%
water: 0.02%

EXAMPLE 2

The reactant feed to the pre-reactor consisted of:
sucrose: 6.23%
KOH: 0.25%
coconut soap (*): 3.15%
soybean methanol ester: 90.33%
water: 0.04%
(*) includes 0.30% of soybean methanol ester derived soap In terms of molar ratios these amounts corresponded to:
KOH:sucrose—0.25:1
soap:sucrose—0.65:1
soybean methanol ester:sucrose—16.8:1

The reaction conditions in the pre-reactor (0.79 kg reaction mixture) were:
temperature: 135° C.
partial methanol pressure: 46 mbar
stirring power input per volume of reaction mixture: 4–5 W/l
stripping gas volume per weight of reactant feed: 268 l/kg (*)
average residence time of reaction mixture in pre-reactor: 1.9 hours
(*) under reaction conditions Reaching steady-state in about 2.5 average residence times after start-up, the composition of the out-going product stream of reaction mixture from the pre-reactor was:
sucrose oligoester (degree of conversion: 25.6%): 16.27%
sucrose: 0.00%
KOH: 0.06%
soap: 4.11%
soybean methanol ester: 79.22%

EXAMPLE 3

The reactant feed to the pre-reactor consisted of:
sucrose: 6.10%
KOH: 0.27%
coconut soap (*): 2.84%
soybean methanol ester: 90.69% water: 0.10%
(*) includes 0.30% of soybean methanol ester derived soap

In terms of molar ratios these amounts corresponded to:
KOH:sucrose—0.27:1
soap:sucrose—0.60:1
soybean methanol ester:sucrose—17.2:1

The reaction conditions in the pre-reactor (0.77 kg reaction mixture) were:
temperature: 135° C.
partial methanol pressure: 42 mbar
stirring power input per volume of reaction mixture: 4–5 W/l
stripping gas volume per weight of reactant feed: 364 l/kg (*)
average residence time of reaction mixture in pre-reactor: 2.0 hours
(*) under reaction conditions Reaching steady-state in about 2.5 average residence times after start-up, the composition of the out-going product stream of reaction mixture from the pre-reactor was:
sucrose oligoester (degree of conversion: 32.2%): 18.50%
sucrose: 0.00%
KOH: 0.04%
soap: 3.82%
soybean methanol ester: 77.01%

EXAMPLE 4

The reactant feed to the pre-reactor consisted of:
sucrose: 6.72%
KOH: 0.48%
coconut soap (*): 3.21%
soybean methanol ester: 89.52%
water: 0.07%
(*) includes 0.3% of soybean methanol ester derived soap In terms of molar ratios these amounts correspond to:
KOH:sucrose—0.44:1
soap:sucrose—0.62:1
soybean methanol ester:sucrose—15.4:1

The reaction conditions in the pre-reactor (0.73 kg reaction mixture) were:
temperature: 136° C.
partial methanol pressure: 42 mbar
stirring power input per volume of reaction mixture: 4–5 W/l
stripping gas volume per weight of reactant feed: 142 l/kg (*)
average residence time of reaction mixture in pre-reactor: 1.8 hours
(*) under reaction conditions Reaching steady-state in about 2.5 average residence times after start-up, the composition of the out-going product stream of reaction mixture from the pre-reactor was:
sucrose oligoester (degree of conversion: 10.3%): 10.73%
sucrose: 0.19%
KOH: 0.13%
soap: 4.67%
soybean methanol ester: 82.82%

EXAMPLE 5

The reactant feed to the pre-reactor consisted of:
sucrose: 6.80%
KOH: 0.31%
coconut soap (*): 3.25%
soybean methanol ester: 89.57%
water: 0.07%
(*) includes 0.3% of soybean methanol ester derived soap In terms of molar ratios these amounts corresponded to:
KOH:sucrose—0.28:1
soap:sucrose—0.62:1
soybean methanol ester:sucrose—15.2:1

The reaction conditions in the pre-reactor (0.77 kg reaction mixture) were:
temperature: 135° C.
partial methanol pressure: 41 mbar
stirring power input per volume of reaction mixture: 4–5 W/l
stripping gas volume per weight of reactant feed: 518 l/kg (*)
average residence time of reaction mixture in pre-reactor: 1.8 hours
(*) under reaction conditions Reaching steady-state in about 2.5 average residence times after start-up, the composition of the out-going product stream of reaction mixture from the pre-reactor was:
sucrose oligoester (degree of conversion: 41.5%): 23.71%
sucrose: 0.28%
KOH: 0.11%
soap: 4.11%
soybean methanol ester: 71.22%

EXAMPLE 6

The reactant feed to the pre-reactor consisted of:
sucrose: 5.99%
KOH: 0.26%
coconut soap (*): 2.07%
soybean methanol ester: 91.63%
water: 0.05%
(*) includes 0.3% of soybean methanol ester derived soap In terms of molar ratios these amounts corresponded to:
KOH:sucrose—0.26:1
soap:sucrose—0.45:1
soybean methanol ester:sucrose—17.7:1

The reaction conditions in the pre-reactor (0.77 kg reaction mixture) were:
temperature: 135° C.
partial methanol pressure: 86 mbar
stirring power input per volume of reaction mixture: 4–5 W/l
stripping gas volume per weight of reactant feed: 95 l/kg (*)
average residence time of reaction mixture in pre-reactor: 1.9 hours
(*) under reaction conditions Reaching steady-state in about 2.5 average residence times after start-up, the composition of the out-going product stream of reaction mixture from the pre-reactor was:
sucrose oligoester (degree of conversion: 20.2%): 12.33%
sucrose: 0.55%
KOH: 0.12%
soap: 2.73%
soybean methanol ester: 83.97%

EXAMPLE 7

The reactant feed to the pre-reactor consisted of:
sucrose: 5.89%
KOH: 0.39%
coconut soap (*): 3.47% soybean methanol ester: 90.17%
water: 0.08%

(*) includes 0.3% of soybean methanol ester derived soap

In terms of molar ratios these amounts corresponded to:
 KOH:sucrose—0.40:1
 soap:sucrose—0.76:1
 soybean methanol ester:sucrose—17.7:1

The reaction conditions in the pre-reactor (88 kg reaction mixture) were:
 temperature: 135° C.
 partial methanol pressure: 50 mbar
 stirring power input per volume of reaction mixture: 4–5 W/l
 stripping gas volume per weight of reactant feed: 166 l/kg (*)
 average residence time of reaction mixture in pre-reactor: 1.9 hours (*) under reaction conditions Reaching steady-state in about 2.5 average residence times after start-up, the composition of the out-going product stream of reaction mixture from the pre-reactor which was fed to the main reactor (identical to the pre-reactor), was:
 sucrose oligoester (degree of conversion: 18.5%): 12.44%
 sucrose: 0.13%
 KOH: 0.12%
 soap: 3.17%
 soybean methanol ester: 83.46%

The reaction conditions in the main reactor (104 kg reaction mixture) were:
 temperature (°C): 136° C.
 average residence time (hours): 2.2 h
 partial methanol pressure (*): 39 mbar (*) stripping gas volume per weight of reactant feed: 261 l/kg The composition of the final product from the main reactor was:
 sucrose polyester (degree of conversion: 40.7%): 20.81%
 sucrose: 0.00%
 KOH: 0.07%
 soap: 5.10%
 soybean methanol ester: 74.00%
 water: 0.02%

EXAMPLE 8

The reactant feed to the pre-reactor consisted of:
 sucrose: 14.05%
 KOH: 0.57%
 coconut soap (*): 5.38%
 soybean methanol ester: 79.86%
 water: 0.14%

(*) includes 0.55% of soybean methanol ester derived soap

In terms of molar ratios these amounts corresponded to:
 KOH: sucrose — 0.25:1
 soap: sucrose — 0.49:1
 soybean methanol ester: sucrose — 6.57:1

The reaction conditions in the pre-reactor (0.64 kg reaction mixture) were:
 temperature: 135° C.
 partial methanol pressure: 42 mbar
 stirring power input per volume of reaction mixture: 4–5 W/l
 stripping gas volume per weight of reactant feed: 602 l/kg (*)
 average residence time of reaction mixture in pre-reactor: 1.7 hours (*) under reaction conditions Reaching steady-state in about 2.5 average residence times after start-up, the composition of the out-going product stream of reaction mixture from the pre-reactor was:
 sucrose oligoester (degree of conversion: 22.8%): 33.89%
 sucrose: 1.22%
 KOH: 0.24%
 soap: 6.87%
 soybean methanol ester: 57.78%

EXAMPLE 9

The reactant feed to the pre-reactor consisted of:
 sucrose: 9.24%
 KOH: 0.36%
 coconut soap (*): 4.32%
 soybean methanol ester: 85.96%
 water: 0.12%

(*) includes 0.45% of soybean methanol ester derived soap

In terms of molar ratios these amounts corresponded to:
 KOH: sucrose — 0.24:1
 soap: sucrose — 0.60:1
 soybean methanol ester: sucrose — 10.7:1

The reaction conditions in the pre-reactor (0.75 kg reaction mixture) were:
 temperature: 136° C.
 partial methanol pressure: 42 mbar
 stirring power input per volume of reaction mixture: 4–5 W/l
 stripping gas volume per weight of reactant feed: 373 l/kg (*)
 average residence time of reaction mixture in pre-reactor: 1.9 hours (*) under reaction conditions Reaching steady-state in about 2.5 average residence times after start-up, the composition of the out-going product stream of reaction mixture from the pre-reactor was:
 sucrose oligoester (degree of conversion: 22.2%): 21.91%
 sucrose: 0.48%
 KOH: 0.09%
 soap: 5.71%
 soybean methanol ester: 71.76%

EXAMPLE 10

The reactant feed to the pre-reactor consisted of:
 sucrose: 5.51%
 KOH: 0.27%
 coconut soap (*) 2.01%
 soybean methanol ester: 92.17%
 water: 0.04%

(*) includes 0.55% of soybean methanol ester derived soap

In terms of molar ratios these amounts corresponded to:
 KOH: sucrose — 0.30:1
 soap: sucrose — 0.47:1
 soybean methanol ester: sucrose — 21.6:1

The reaction conditions in the pre-reactor (0.90 kg reaction mixture) were:
 temperature: 136° C.
 partial methanol pressure: 45 mbar
 stirring power input per volume of reaction mixture: 4–5 W/l
 stripping gas volume per weight of reactant feed: 155 l/kg (*)

average residence time of reaction mixture in pre-reactor: 2.5 hours
(*) under reaction conditions Reaching steady-state in about 2.5 average residence times after start-up, the composition of the out-going product stream of reaction mixture from the pre-reactor which was fed to the main reactor (identical to the pre-reactor), was:
  sucrose oligoester (degree of conversion: 18.5%): 10.23%
  sucrose: 0.83%
  KOH: 0.09%
  soap: 2.70%
  soybean methanol ester: 86.22%

The reaction conditions in the main reactor (0.51 kg reaction mixture) were:
  temperature (°C.): 135° C.
  average residence time (hours): 1.4 h
  partial methanol pressure (*): 16 mbar
(*) stripping gas volume per weight of reactant feed: 1315 l/kg The composition of the final product from the main reactor was:
  sucrose polyester (degree of conversion: 67.0%): 27.36%
  sucrose: 0.26%
  KOH: 0.07%
  soap: 3.53%
  soybean methanol ester: 68.79%

EXAMPLE 11

The reactant feed to the pre-reactor consisted of:
  sucrose: 7.50%
  KOH: 0.31%
  coconut soap (*): 2.80%
  soybean methanol ester: 89.33%
  water: 0.06%
(*) includes 0.3% of soybean methanol ester derived soap In terms of molar ratios these amounts corresponded to:
  KOH: sucrose — 0.25:1
  soap: sucrose — 0.48:1
  soybean methanol ester: sucrose — 13.8:1

The reaction conditions in the pre-reactor (0.74 kg reaction mixture) were:
  temperature: 135° C.
  partial methanol pressure: 51 mbar
  stirring power input per volume of reaction mixture: 4-5 W/l
  stripping gas volume per weight of reactant feed: 310 l/kg (*)
  average residence time of reaction mixture in pre-reactor: 1.9 hours
(*) under reaction conditions Reaching steady-state in about 2.5 average residence times after start-up, the composition of the out-going product stream of reaction mixture from the pre-reactor was:
  sucrose oligoester (degree of conversion: 27.1%): 19.97%
  sucrose: 1.14%
  KOH: 0.12%
  soap: 3.81%
  soybean methanol ester: 74.96%

I claim:

1. A process for the synthesis of polyol fatty-acid esters by reacting a polyol and a fatty-acid lower-alkyl ester under substantially solvent free conditions in the presence of a transesterification catalyst and an emulsifier, the process comprising an initial reaction stage (a) which is carried out in a first reaction zone under such conditions that the reaction mixture in said first zone is in steady-state with massbalanced one or more in-going reactant streams into said first zone and out-going product streams from said first zone, said one or more in-going reactant streams comprising polyol and fatty-acid lower-alkyl ester, and said out-going product streams comprising reaction mixture having a polyol conversion of 1% or more and lower-alkyl alcohol formed during the initial stage of the synthesis, and a subsequent reaction stage (b) in which the reaction mixture from said first zone is further reacted to said polyol fatty-acid esters in one or more subsequent reaction zones.

2. The process according to claim 1 wherein the reaction mixture from the first zone is further reacted to said polyol fatty acid esters after combining with any remaining part of reactants.

3. A process according to claim 1 wherein the emulsifier is an alkali metal soap.

4. A process according to claim 3 wherein the alkali metal soap is selected from the group of short chain soaps having a chain length within the range of from 6 to 14 carbon atoms.

5. A process according to claim 1 wherein the fatty-acid lower-alkyl ester is a fatty-acid methyl ester.

6. A process according to claim 1 wherein the transesterification catalyst is selected from the group consisting of hydroxides, carbonates and bicarbonates of potassium and sodium.

7. A process according to claim 1 wherein the reaction mixture in said first reaction zone has a degree of polyol conversion of within the range of from 10 to 40%.

8. A process according to claim 1 wherein the reaction mixture in said first zone has a solvent level of 0.1% by weight or less.

9. A process according to claim 1 wherein the reaction temperature in said first zone is maintained at a level of within the range of from 120° to 150° C.

10. A process according to claim 1 wherein the partial vapour pressure of the fatty-acid lower-alkyl ester in said first reaction zone is reduced to a level of within the range of from 40 to 125 mbar.

11. A process according to claim 10 wherein the partial vapour pressure is reduced by the use of a stripping agent.

12. A process according to claim 11 wherein the stripping agent is used in an amount within the range of from 60 to 300 liters per kg of reaction mixture.

13. A process according to claim 1 wherein the average residence time of the reaction mixture in said first zone is caused to be within the range of from 1.5 to 2.5 hours.

14. A process according to claim 1 wherein the molar ratio of transesterification catalyst to polyol in said first reaction zone is within the range of from 0.1:1 to 0.3:1.

15. A process according to claim 1 wherein the molar ratio of emulsifier to polyol in said first reaction zone is within the range of from 0.2:1 to 0.8:1.

16. A process according to claim 1 for the synthesis of polyol fatty-acid polyesters.

17. A process according to claim 16 for the synthesis of polyol fatty-acid polyesters having a polyol conversion of 90% or more.

18. A process according to claim 1 wherein the polyol is sucrose.

19. A process according to claim 18 wherein the molar ratio of fatty-acid lower-alkyl ester to sucrose is within the range of from 10.5:1 to 18:1.

20. A process according to claim 1 wherein said first reaction zone is fully separate from said one or more subsequent reaction zones.

21. A process according to claim 1 wherein said one or more subsequent reaction zones are compartments of a multi-tray column reactor.

* * * * *

REEXAMINATION CERTIFICATE (3502nd)

United States Patent [19]

Buter

[11] B1 5,043,438

[45] Certificate Issued Apr. 28, 1998

[54] PROCESS FOR THE SYNTHESIS OF POLYOL FATTY-ACID ESTERS

[75] Inventor: Markus G. Buter, Vlaardingen, Netherlands

[73] Assignee: Lever Brothers Company, New York, N.Y.

Reexamination Requests:
No. 90/002,711, May 1, 1992
No. 90/003,072, May 27, 1993
No. 90/004,646, May 22, 1997

Reexamination Certificate for:
Patent No.: 5,043,438
Issued: Aug. 27, 1991
Appl. No.: 477,776
Filed: Feb. 9, 1990

[30] Foreign Application Priority Data

Feb. 16, 1989 [EP] European Pat. Off. ............ 89200371.6
Nov. 20, 1989 [EP] European Pat. Off. ............ 89202931.5

[51] Int. Cl.$^6$ .................... C07H 13/00; C07H 1/00; C11C 3/00
[52] U.S. Cl. .................... 536/119; 536/115; 536/120; 536/124
[58] Field of Search .................... 536/119, 115, 536/120, 124

[56] References Cited

U.S. PATENT DOCUMENTS

| | | |
|---|---|---|
| 3,714,144 | 1/1973 | Fuege . |
| 3,963,699 | 6/1976 | Rizzi et al. . |
| 4,298,730 | 11/1981 | Galleymore . |
| 4,517,360 | 5/1985 | Volpenhein . |
| 4,518,772 | 5/1985 | Volpenhein . |
| 4,611,055 | 9/1986 | Yamamoto et al. . |
| 4,778,881 | 10/1988 | Nieuwenhuis et al. . |
| 4,973,682 | 11/1990 | Willemse . |
| 5,144,023 | 9/1992 | Willemse . |
| 5,231,199 | 7/1993 | Willemse . |

FOREIGN PATENT DOCUMENTS

| | | |
|---|---|---|
| 0 190 779 | 1/1985 | European Pat. Off. . |
| 0 256 585 | 7/1986 | European Pat. Off. . |
| 254376 | 1/1988 | European Pat. Off. . |
| 0 301 634 | 7/1988 | European Pat. Off. . |
| 0 315 265 | 10/1988 | European Pat. Off. . |
| 0 320 043 | 11/1988 | European Pat. Off. . |
| 0 322 971 | 7/1989 | European Pat. Off. . |
| 25 03 195 | 7/1976 | Germany . |
| 2503195 | 7/1976 | Germany . |
| 50-135-016 | 10/1975 | Japan . |
| 1250204 | 12/1967 | United Kingdom . |

OTHER PUBLICATIONS

Rizzi and Taylor, "A Solvent–Free Synthesis Of Sucrose Polyesters," *Journal of the American Oil the American Oil Chemist's Society*, vol. 55, pp. 398–401 (1978).

Fuege, Zeringue, Weiss and Brown, "Preparation of Sucrose Esters By Interesterification," *Journal of the American Oil Chemists' Society*, vol. 47, pp. 56–60 (1970).

Felder, et al. *Elementary Principles of Chemical Process*, p. 82 (Wiley 1978).

McCabe and Smith, *Unit Operations of Chemical Engineering*, 3d Ed., p. 66 (McGraw-Hill, 1976).

Kirk–Othmer, *Encyclopedia Of Chemical Technology Third Edition*, vol. 19, pp. 880–883 (John Wiley & Sons, 1982).

*McGraw–Hill Dictionary Of Scientific And Technical Terms Third Edition*, p. 1337 (McGraw-Hill, 1984).

Westerterp et al., *Chemical Reactor Design And Operation*, pp. 38, 97–98, 115 (John Wiley & Sons, 1987).

Lemieux & McInnes, *Canadian J. Chem.* 40:2376–93 (1962).

Nam & Sohn, *J. Korean Chem. Soc'y* 25(4): 233–290 (1981).

Carberry, *Chemical and Catalytic Reaction Engineering*, p. 31 (McGraw– Hill (1976).

Levenspiel, *Chemical Reaction Engineering*, pp. 97–98 (John Wiley & Sons, 1992).

*Perry's Chemical Engineer's Handbook Sixth Edition*, Table 3–8 (McGraw-Hill 1993).

Rizzi et al., *JAOCS* 55(4): 398–401 (1978).

Feuge et al., *JAOCS* 47: 56–60 (1970).

Felder & Rosseau, *Elementary Principles of Chemical Processes*, p. 82 (John Wiley & Sons, 1978).

McCabe & Smith, *Unit Operations of Chemical Engineering 3d Edition*, chapter 4, first page (McGraw Hill, 1976).

Jul. 2, 1997 Notice of Opposition to European Patent No. 0,303,404.

*Primary Examiner*—John Kight, III

[57] ABSTRACT

The present invention pertains to a process for the synthesis of polyol fatty-acid esters by reacting a polyol and a fatty-acid lower-alkyl ester under substantially solvent-free conditions in the presence of a transesterification catalyst and an emulsifier. The process comprises a continuous initial reaction stage in a first reaction zone wherein a steady-state conversion is achieved of over 1% and a further reaction stage in which the reaction mixture from said first zone is further reacted to the required polyol fatty-acid esters in one or more subsequent reaction zones.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–9 and 13–21 is confirmed.

Claim 10 is determined to be patentable as amended.

Claims 11–12, dependent on an amended claim, are determined to be patentable.

New claims 22–73 are added and determined to be patentable.

10. A process according to claim 1 wherein the partial vapour pressure of the [fatty acid] lower-alkyl [ester] *alcohol* in said first reaction zone is reduced to a level of within the range of from 40 to 125 mbar.

22. *The process according to claim 1 wherein the emulsifier is used in the first reaction zone in an amount of from 1 to 4% by weight of the reactant mixture.*

23. *The process according to claim 1 wherein the initial reaction stage is carried out in a continuous reaction vessel having stirring means and having a suction line for the outgoing product stream and an inlet portion for the suction line such that all fluids above a certain point are removed.*

24. *The process according to claim 23 wherein said reaction vessel is provided with inlets and outlets for a stripping agent.*

25. *The process according to claim 23 wherein in the first reaction zone the stirring means applies agitation to ensure thorough mixing of the reaction components.*

26. *The process according to claim 1 wherein the initial reaction stage is carried out in a continuous flow stirred tank reactor.*

27. *The process according to claim 1 wherein the steady state reaction mixture in the first zone is capable of homogenizing and solubilizing the in-going stream of reactants.*

28. *A process according to claim 1 for the synthesis of polyol fatty-acid polyesters having a polyol conversion of 70% or more.*

29. *A process according to claim 1 for the synthesis of polyol fatty-acid polyesters having a polyol conversion of 80% or more.*

30. *A process according to claim 1 for the synthesis of polyol fatty-acid polyesters having a polyol conversion of 90% or more.*

31. *A process according to claim 1 for the synthesis of polyol fatty-acid polyesters having a polyol conversion of 95% or more.*

32. *A process according to claim 1 for the synthesis of polyol fatty-acid polyesters having a polyol conversion of 98% or more.*

33. *A process for the synthesis of polyol fatty-acid esters by reacting a polyol and a fatty-acid lower-alkyl ester of a monoalcohol under substantially solvent free conditions in the presence of a transesterification catalyst and an emulsifier, the process comprising an initial reaction stage (a) which is carried out in a first reaction zone under such conditions that the reaction mixture in said first zone is in steady-state with massbalanced one or more in-going reactant streams into said first zone and out-going product streams from said first zone, said one or more in-going reactant streams comprising polyol and fatty-acid lower-alkyl ester of a monoalcohol, and said out-going product streams comprising reaction mixture having a polyol conversion of 1% or more and lower-alkyl alcohol formed during the initial stage of the synthesis, and a subsequent reaction stage (b) in which the reaction mixture from said first zone is further reacted to said polyol fatty-acid esters in one or more subsequent reaction zones.*

34. *The process according to claim 33 wherein the fatty-acid lower-alkyl ester of a monoalcohol is a fatty-acid methyl ester.*

35. *The process according to claim 33 wherein there is one ingoing reactant stream.*

36. *The process according to claim 33 wherein the emulsifier is used in the first reaction zone in an amount of from 1 to 4% by weight of the reactant mixture.*

37. *A process for the synthesis of polyol fatty-acid esters by reacting a polyol and a fatty-acid lower-alkyl ester under substantially solvent free conditions in the presence of a transesterification catalyst selected from the group consisting of alkali metals, alkaline earth metals, and alloys, alkoxides, bicarbonates, carbonates, hydrides, and hydroxides thereof, and an emulsifier, the process comprising an initial reaction stage (a) which is carried out in a first reaction zone under such conditions that the reaction mixture in said first zone is in steady-stage with massbalanced one or more in-going reactant streams into said first zone and out-going product streams from said first zone, said one or more in-going reactant streams comprising polyol and fatty-acid lower-alkyl ester, and said out-going product streams comprising reaction mixture having a polyol conversion of 1% or more and lower-alkyl alcohol formed during the initial stage of the synthesis, and a subsequent reaction stage (b) in which the reaction mixture from said first zone is further reacted to said polyol fatty-acid esters in one or more subsequent reaction zones.*

38. *The process according to claim 37 wherein said fatty acid lower alkyl esters are esters of monoalcohols.*

39. *The process of claim 37 wherein the transesterification catalyst is selected from the group consisting of sodium hydroxide, potassium hydroxide, sodium carbonate and potassium carbonate.*

40. *A process for the synthesis of polyol fatty-acid esters by reacting a polyol and a fatty-acid lower-alkyl ester under substantially solvent free conditions in the presence of a transesterification catalyst and an emulsifier, the process comprising an initial reaction stage (a) which is carried out in a first reaction zone under such conditions that the reaction mixture in said first zone is in steady-state with massbalanced one or more in-going reactant streams into said first zone and out-going product streams from said first zone, said one or more in-going reactant streams comprising polyol and fatty-acid lower-alkyl ester, and said out-going product streams comprising reaction mixture having a polyol conversion of 10% or more and lower-alkyl alcohol formed during the initial stage of the synthesis, and an subsequent reaction stage (b) in which the reaction mixture from said first zone is further reacted to said polyol fatty-acid esters in one or more subsequent reaction zones.*

41. *The process of claim 40 wherein said fatty acid lower alkyl esters are esters of monoalcohols.*

42. The process of claim 41 wherein the transesterification catalyst is selected from the group consisting of alkali metals, alkaline earth metals, and alloys, alkoxides, bicarbonates, carbonates, hydrides, and hydroxides thereof.

43. The process according to claim 42 wherein the polyol is sucrose and the molar ratio of fatty-acid lower-alkyl ester to sucrose in the in-going reactant stream is within the range of from 10.5:1 to 18:1.

44. The process according to claim 42 wherein the full amount of the fatty-acid lower-alkyl ester is introduced into the first reaction zone.

45. The process according to claim 44 for synthesis of polyol fatty acid polyesters.

46. The process according to claim 42 wherein from 1 to 4% soap is introduced in the first reaction zone.

47. The process according to claim 42 wherein the emulsifier introduced into the first reaction zone is soap.

48. The process according to claim 47 wherein the polyol is sucrose and the unreacted sucrose in the outgoing product stream from said first zone is 15% or less of the sucrose in the reactant mixture.

49. The process according to claim 48 wherein the first reaction zone temperature is maintained at a level of within the range from 120° to 150° C.

50. The process according to claim 49 wherein the initial reaction stage is carried out in a continuous flow stirred tank reactor.

51. The process according to claim 49 wherein the initial reaction stage is carried out in a continuous reaction vessel having stirring means and having a suction line for the outgoing product stream and an inlet point for the suction line such that all fluids above a certain point are removed.

52. The process of claim 41 wherein the transesterification catalyst is selected from the group consisting of sodium hydroxide, potassium hydroxide, sodium carbonate and potassium carbonate.

53. The process of claim 52 for synthesis of polyol fatty acid polyesters.

54. The process of claim 41 wherein the first reaction zone steady state polyol conversations lie within the range of from 10 to 60%.

55. The process according to claim 40 wherein the initial reaction stage is carried out in a continuous reaction vessel having stirring means and having suction line for the outgoing product stream and an inlet point for the suction line such that all fluids above a certain point are removed, said polyol conversions in said first reaction zone lying within a range of from 10–60%, said fatty acid lower alkyl esters are esters of monoalcohols and the process results in synthesis of polyesters.

56. The process according to claim 55 wherein said reaction vessel is provided within inlets and outlets for a stripping agent.

57. The process according to claim 55 wherein in the first reaction zone the stirring means applies agitation to ensure thorough mixing of the reaction components.

58. The process according to claim 57 wherein the first reaction zone temperature is maintained at a level of within the range of from 120° to 150° C.

59. The process according to claim 40 wherein the initial reaction stage is carried out in a continuous flow stirred tank reactor.

60. The process of claim 59 wherein said fatty acid lower alkyl esters are esters of monoalcohols.

61. The process of claim 60 wherein the transesterification catalyst is selected from the group consisting of alkali metals, alkaline earth metals, and alloys, alkoxides, bicarbonates, carbonates, hydrides, and hydroxides thereof.

62. The process according to claim 61 wherein the first reaction zone temperature is maintained at a level of within the range of from 120° to 150° C.

62. The process according to claim 62 wherein the emulsifier is a soap.

64. The process according to claim 63 wherein polyol fatty acid polyesters are prepared.

65. A process for the synthesis of polyol fatty-acid esters by reacting a polyol and a fatty-acid lower alkyl ester under substantially solvent free conditions in the presence of a transesterification catalyst selected from the group consisting of alkali metals, alkaline earth metals, and alloys, alkoxides, bicarbonates, carbonates, hydrides, and hydroxides thereof, and an emulsifier, the process comprising an initial reaction stage (a) which is carried out in a first reaction zone the temperature of which is maintained at a level of within the range of from 120° to 150° C. under such conditions that the reaction mixture in said first zone is in steady-state with massbalance one or more in-going reactant streams into said first zone and out-going product streams from said first zone, said one or more in-going reactant streams comprising polyol and fatty-acid lower-alkyl ester of a monoalcohol, and said out-going product streams comprising reaction mixture having a polyol conversion of 10% or more and lower-alkyl alcohol formed during the initial stage of the synthesis, and a subsequent reaction stage (b) in which the reaction mixture from said first zone is further reacted to said polyol fatty-acid esters in one or more subsequent reaction zone.

66. The process according to claim 65 wherein the emulsifier is used in the first reaction zone in an amount of from 1 to 4% by weight of the reactant mixture.

67. A process for the synthesis of polyol fatty-acid esters by reacting a polyol and a fatty-acid lower-alkyl ester under substantially solvent free conditions in the presence of a transesterification catalyst and an emulsifier, the process comprising an initial reaction stage (a) which is carried out in a first reaction zone under such conditions that the reaction mixture in said first zone is in steady-state with mass-balanced one or more in-going reactant streams into said first zone and out-going product streams from said first zone, said one or more in-going reactant streams comprising polyol and fatty-acid lower alkyl ester, and said out-going product streams comprising reaction mixture having a polyol conversion of 1% or more and lower-alkyl alcohol formed during the initial stage of the synthesis, such conditions being effective, on an average, to overcome substantially de-mixing of the reactant mixture, and a subsequent reaction (b) in which the reaction mixture from said first zone is further reacted to said polyol fatty-acid esters in one or more subsequent reaction zones.

68. A process for the synthesis of polyol fatty-acid esters by reacting a polyol and a fatty-acid lower-alkyl ester under substantially solvent free conditions in the presence of a transesterification catalyst and an emulsifier, the process comprising an initial reaction stage (a) which is carried out in a first reaction zone under such conditions that the reaction mixture in said first zone is in steady-state with mass-balanced one or more in-going reactant streams into said first zone and out-going product strams from said first zone, said one or more in-going reactant streams comprising polyol and fatty-acid lower alkyl ester, and said out-going product streams comprising reaction mixture having a polyol conversion of 1% or more and lower-alkyl alcohol formed during the initial stage of the synthesis, such conditions being effective, on an average, to overcome substantially high viscosities during the polyol conversion, and a subsequent reaction (b) in which the reaction mixture from said first zone is further reacted to said polyol fatty-acid esters in one or more subsequent reaction zones.

69. A process for the synthesis of polyol fatty-acid esters by reacting a polyol and a fatty-acid lower-alkyl ester under substantially solvent free conditions in the presence of a transesterification catalyst and an emulsifier, the process comprising an initial reaction stage (a) which is carried out in a first reaction zone under such conditions that the reaction mixture in said first zone is in steady-state with mass-balanced one or more in-going reactant streams into said first zone and out-going product streams from said first zone, said one or more in-going reactant streams comprising polyol and fatty-acid lower alkyl ester, and said out-going product streams comprising reaction mixture having a polyol conversion of 1% or more and lower-alkyl alcohol formed during the initial stage of the synthesis, such conditions being effective to render the steady-state reaction mixture capable of homogenizing and solubilizing said in-going reactant streams, and a subsequent reaction (b) in which the reaction mixture from said first zone is further reacted to said polyol fatty-acid esters in one or more subsequent reaction zones.

70. A process for the synthesis of polyol fatty-acid esters by reacting a polyol and a fatty-acid lower-alkyl ester under substantially solvent free conditions in the presence of a transesterification catalyst and an emulsifier, the process comprising an initial reaction stage (a) which is carried out in a first reaction zone under such conditions that the reaction mixture in said first zone is in steady-state with mass-balanced one or more in-going reactant streams into said first zone and out-going product streams from said first zone, said one or more in-going reactant streams comprising polyol and fatty-acid lower alkyl ester, and said out-going product streams comprising reaction mixture having a polyol conversion of 1% or more and lower-alkyl alcohol formed during the initial stage of the synthesis, such conditions being effective, on an average, i) to overcome substantially de-mixing of the reactant mixture and ii) high viscosities during the polyol conversion, and a subsequent reaction (b) in which the reaction mixture from said first zone is further reacted to said polyol fatty-acid esters in one or more subsequent reaction zones.

7. A process for the synthesis of polyol fatty-acid esters by reacting a polyol and a fatty-acid lower-alkyl ester under substantially solvent free conditions in the presence of a transesterification catalyst and an emulsifier, the process comprising an initial reaction stage (a) which is carried out in a first reaction zone under such conditions that the reaction mixture in said first zone is in steady-state with mass-balanced one or more in-going reactant streams into said first zone and out-going product streams from said first zone, said one or more in-going reactant streams comprising polyol and fatty-acid lower alkyl ester, and said out-going product streams comprising reaction mixture having a polyol conversion of 1% or more and lower-alkyl alcohol formed during the initial stage of the synthesis, such conditions being effective i) to overcome substantially, on an average, de-mixing of the reactant mixture and ii) to render the steady-state reaction capable of homogenizing and solubilizing said in-going reactant streams, and a subsequent reaction (b) in which the reaction mixture from said first zone is further reacted to said polyol fatty-acid esters in one or more subsequent reaction zones.

72. A process for the synthesis of polyol fatty-acid esters by reacting a polyol and a fatty-acid lower-alkyl ester under substantially solvent free conditions in the presence of a transesterification catalyst and an emulsifier, the process comprising an initial reaction stage (a) which is carried out in a first reaction zone under such conditions that the reaction mixture in said first zone is in steady-state with mass-balanced one or more in-going reactant streams into said first zone and out-going product streams from said first zone, said one or more in-going reactant streams comprising polyol and fatty-acid lower alkyl esters, and said out-going product streams comprising reaction mixture having a polyol conversion of 1% or more and lower-alkyl alcohol formed during the initial stage of the synthesis, such conditions being effective i) to overcome substantially, on an average, high viscosities during the polyol conversion and ii) to render the steady-state reaction mixture capable of homogenizing and solubilizing said in-going reactant streams, and a subsequent reaction (b) in which the reaction mixture from said first zone is further reacted to said polyol fatty-acid esters in one or more subsequent reaction zones.

73. A process for the synthesis of polyol fatty-acid esters by reacting a polyol and a fatty-acid lower-alkyl ester under substantially solvent free conditions in the presence of a transesterification catalyst and an emulsifier, the process comprising an initial reaction stage (a) which is carried out in a first reaction zone under such conditions that the reaction mixture in said first zone is in steady-state with mass-balanced one or more in-going reactant streams into said first zone and out-going product streams from said first zone, said one or more in-going reactant streams comprising polyol and fatty-acid lower alkyl ester, and said out-going product streams comprising reaction mixture having a polyol conversion of 1% or more and lower-alkyl alcohol formed during the initial stage of the synthesis, such conditions being effective i) to overcome substantially, on an average, de-mixing of the reactant mixture and high viscosities during the polyol conversion and ii) to render the steady-state reaction mixture capable of homogenizing and solubilizing said in-going reactant streams, and a subsequent reaction (b) in which the reaction mixture from said first zone is further reacted to said polyol fatty-acid esters in one or more subsequent reaction zones.

* * * * *